US010765612B2

(12) United States Patent
Fameau et al.

(10) Patent No.: US 10,765,612 B2
(45) Date of Patent: Sep. 8, 2020

(54) DYE COMPOSITION COMPRISING 12-HYDROXYSTEARIC ACID, AN ORGANIC AMINE AND A DYE

(71) Applicant: L'OREAL, Paris (FR)

(72) Inventors: Anne-Laure Fameau, Saint-Ouen (FR); Koudedji Sow, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/463,921

(22) PCT Filed: Nov. 27, 2017

(86) PCT No.: PCT/EP2017/080470
§ 371 (c)(1),
(2) Date: May 24, 2019

(87) PCT Pub. No.: WO2018/096132
PCT Pub. Date: May 31, 2018

(65) Prior Publication Data
US 2019/0374452 A1 Dec. 12, 2019

(30) Foreign Application Priority Data
Nov. 28, 2016 (FR) ..................................... 16 61587

(51) Int. Cl.
*A61Q 5/10* (2006.01)
*A61K 8/365* (2006.01)
*A61K 8/22* (2006.01)
*A61K 8/23* (2006.01)
*A61K 8/34* (2006.01)
*A61K 8/41* (2006.01)
*A61K 8/43* (2006.01)
*A61K 8/44* (2006.01)
*A61K 8/46* (2006.01)

(52) U.S. Cl.
CPC ................ *A61K 8/365* (2013.01); *A61K 8/22* (2013.01); *A61K 8/23* (2013.01); *A61K 8/347* (2013.01); *A61K 8/411* (2013.01); *A61K 8/415* (2013.01); *A61K 8/43* (2013.01); *A61K 8/44* (2013.01); *A61K 8/463* (2013.01); *A61Q 5/10* (2013.01); *A61K 2800/4324* (2013.01); *A61K 2800/592* (2013.01); *A61K 2800/87* (2013.01); *A61K 2800/882* (2013.01)

(58) Field of Classification Search
CPC .......... A61Q 5/10; A61Q 5/065; A61K 8/411; A61K 8/22; A61K 8/41; A61K 8/347; A61K 8/365; A61K 8/361; A61K 8/362; A61K 2800/882; A61K 2800/87; A61K 2800/88; A61K 8/4926; A61K 2800/4324; A61K 8/44; A61K 8/415
See application file for complete search history.

(56) References Cited

U.S. PATENT DOCUMENTS

| | | |
|---|---|---|
| 3,869,454 A | 3/1975 | Lang et al. |
| 3,955,918 A | 5/1976 | Lang |
| 4,003,699 A | 1/1977 | Rose et al. |
| 4,025,301 A | 5/1977 | Lang |
| 4,165,239 A | 8/1979 | Linden et al. |
| RE30,199 E | 1/1980 | Rose et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Möckli |
| 5,766,576 A | 6/1998 | Löwe et al. |
| 6,099,592 A | 8/2000 | Vidal et al. |
| 6,284,003 B1 | 9/2001 | Rose et al. |
| 6,554,872 B2 | 4/2003 | Genet et al. |
| 6,730,789 B1 | 5/2004 | Birault et al. |
| 6,881,230 B2 | 4/2005 | Vidal |
| 6,884,265 B2 | 4/2005 | Vidal et al. |
| 6,884,266 B2 | 4/2005 | Vidal et al. |
| 6,893,471 B2 | 5/2005 | Vidal |
| 7,001,436 B2 | 2/2006 | Vidal et al. |
| 7,022,143 B2 | 4/2006 | Vidal et al. |
| 7,060,110 B2 | 6/2006 | Vidal et al. |
| 7,261,743 B2 | 8/2007 | Plos et al. |
| 7,311,736 B2 | 12/2007 | Burgaud et al. |
| 7,407,516 B2 | 8/2008 | Vidal |
| 7,870,633 B2 | 1/2011 | Thiebaut |
| 2005/0196367 A1 | 9/2005 | Ohta et al. |
| 2006/0156479 A1 | 7/2006 | Hercouet et al. |
| 2006/0156488 A1 | 7/2006 | David et al. |
| 2006/0156489 A1 | 7/2006 | David et al. |
| 2006/0156490 A1 | 7/2006 | David et al. |
| 2006/0174422 A1 | 8/2006 | David et al. |
| 2008/0168607 A1 | 7/2008 | David et al. |
| 2010/0154135 A1* | 6/2010 | Matsunaga ............ A61K 8/361 8/406 |
| 2013/0142748 A1* | 6/2013 | Tamura .................. A61K 8/891 424/70.12 |

FOREIGN PATENT DOCUMENTS

| | | |
|---|---|---|
| DE | 2359399 A1 | 6/1975 |
| DE | 3843892 A1 | 6/1990 |
| DE | 4133957 A1 | 4/1993 |
| DE | 19543988 A1 | 5/1997 |
| EP | 0714954 A2 | 6/1996 |
| EP | 0770375 A1 | 5/1997 |
| EP | 1006153 A1 | 6/2000 |
| EP | 1377261 A1 | 1/2004 |
| EP | 1377262 A1 | 1/2004 |
| EP | 1377263 A2 | 1/2004 |
| EP | 1377264 A1 | 1/2004 |
| EP | 1378544 A2 | 1/2004 |
| EP | 1399116 A1 | 3/2004 |
| EP | 1399117 A1 | 3/2004 |

(Continued)

OTHER PUBLICATIONS

International Search Report for counterpart Application No. PCT/EP2017/080470, dated Feb. 16, 2018.

*Primary Examiner* — Eisa B Elhilo
(74) *Attorney, Agent, or Firm* — The Marbury Law Group, PLLC

(57) ABSTRACT

Dye composition comprising 12-hydroxystearic acid, an organic amine and a dye The invention relates to a dye composition comprising 12-hydroxystearic acid, one or more organic amines and one or more dyes chosen from oxidation dyes and direct dyes. The invention also relates to a dyeing process using said dye composition.

17 Claims, No Drawings

(56) References Cited

FOREIGN PATENT DOCUMENTS

| | | | |
|---|---|---|---|
| EP | 1399425 | A1 | 3/2004 |
| EP | 1408919 | A2 | 4/2004 |
| EP | 1416909 | A2 | 5/2004 |
| EP | 1433471 | A1 | 6/2004 |
| EP | 1433472 | A1 | 6/2004 |
| EP | 1433473 | A1 | 6/2004 |
| EP | 1433474 | A1 | 6/2004 |
| EP | 1619220 | A1 | 1/2006 |
| EP | 1619221 | A1 | 1/2006 |
| EP | 1634926 | A1 | 3/2006 |
| EP | 1637566 | A1 | 3/2006 |
| EP | 1671560 | A1 | 6/2006 |
| EP | 1671951 | A1 | 6/2006 |
| EP | 1671952 | A1 | 6/2006 |
| EP | 1671954 | A1 | 6/2006 |
| EP | 1671955 | A1 | 6/2006 |
| EP | 1671971 | A1 | 6/2006 |
| EP | 1672033 | A2 | 6/2006 |
| EP | 1674073 | A1 | 6/2006 |
| EP | 1679312 | A2 | 7/2006 |
| FR | 2140205 | A1 | 1/1973 |
| FR | 2189006 | A1 | 1/1974 |
| FR | 2285851 | A1 | 4/1976 |
| FR | 2733749 | A1 | 11/1996 |
| FR | 2801308 | A1 | 5/2001 |
| FR | 2886136 | A1 | 12/2006 |
| GB | 1026978 | A | 4/1966 |
| GB | 1153196 | A | 5/1969 |
| JP | S59-227999 | | 12/1984 |
| JP | 02-019576 | A | 1/1990 |
| JP | 05-163124 | A | 6/1993 |
| WO | 94/08969 | A1 | 4/1994 |
| WO | 94/08970 | A1 | 4/1994 |
| WO | 95/01772 | A1 | 1/1995 |
| WO | 95/15144 | A1 | 6/1995 |
| WO | 96/15765 | A1 | 5/1996 |
| WO | 2006/063866 | A1 | 6/2006 |
| WO | 2006/063867 | A2 | 6/2006 |
| WO | 2006/063868 | A1 | 6/2006 |
| WO | 2006/063869 | A2 | 6/2006 |

\* cited by examiner

DYE COMPOSITION COMPRISING 12-HYDROXYSTEARIC ACID, AN ORGANIC AMINE AND A DYE

CROSS REFERENCE TO RELATED APPLICATION

This is a national stage application of PCT/EP2017/080470, filed internationally on Nov. 27, 2017, which claims priority to French Application No. 1661587, filed on Nov. 28, 2016, both of which are incorporated by reference herein in their entireties.

The present invention relates to a dye composition comprising 12-hydroxystearic acid, at least one organic amine and at least one dye, to a ready-to-use composition and to a kit comprising said dye composition, and to a dyeing process using said dye composition.

Many people have for a long time sought to modify the colour of their hair, and in particular to dye it, for example in order to mask their grey hair.

In order to dye human keratin fibres durably, "permanent" dyeing methods, also known as oxidation dyeing, have been developed. These methods use dye compositions containing oxidation dye precursors, generally known as oxidation bases, such as ortho- or para-phenylenediamines, ortho- or para-aminophenols and heterocyclic compounds. These oxidation bases are colourless or weakly coloured compounds, which, when combined with oxidizing products, may give rise to coloured compounds via a process of oxidative condensation.

It is also known that the shades obtained with these oxidation bases may be varied by combining them with couplers or colour modifiers, the latter being chosen especially from aromatic meta-diaminobenzenes, meta-aminophenols, meta-diphenols and certain heterocyclic compounds such as indole compounds.

The second type of dyeing is "semi-permanent" dyeing or direct dyeing, which consists in applying, to the keratin fibres, direct dyes, which are coloured and colouring molecules that have affinity for said fibres, in leaving them on for a time, and then in rinsing them off.

In order to perform these dyeing operations, the direct dyes generally used are chosen from nitrobenzene, anthraquinone, nitropyridine, azo, xanthene, acridine, azine and triarylmethane direct dyes, and natural dyes.

Compositions containing one or more direct dye(s) are applied to the keratin fibres for a time necessary to obtain the desired colouring, and are then rinsed off.

The colourings that result therefrom are generally chromatic colourings which are, however, temporary or semi-permanent since the nature of the interactions that bind the direct dyes to the keratin fibre and their desorption from the surface and/or the core of the fibre are responsible for their weak dyeing power and their poor persistence with respect to washing or perspiration.

To improve this direct dyeing, it has been proposed to perform it as oxidation dyeing in the presence of oxidizing agents. This is then referred to as lightening direct dyeing.

The dye compositions are generally in the form of solutions, gels or more or less fluid creams. However, the working qualities and the stability of these compositions remain to be improved. Now, users of cosmetic products are in search of products that are pleasant to use, which spread well, rinse out easily and are stable, especially on storage.

The Applicant has now discovered that a dye composition comprising 12-hydroxystearic acid, at least one organic amine and at least one dye as defined below, used in a dyeing process, makes it possible to obtain a texture with good working qualities, especially in terms of ease of application and ease of rinsing, whether it is used alone, sequentially or as a mixture with an oxidizing composition.

This dye composition shows improved stability over time. It is easy to use, i.e. it can especially be spread easily from the roots to the ends and is easy to rinse out, and thus has a reduced impact on the environment (less consumption of water), while at the same time having good dyeing properties especially in terms of intensity, build-up and selectivity.

For the purposes of the present invention, the term "stable over time" means that the visual appearance and the viscosity of the compositions do not change or do not substantially change (variation generally less than 10% relative to the viscosity at T0) over time under standard or non-standard storage conditions, for example for one month or two months following the manufacture of said compositions, at 4° C., at room temperature (20-25° C.), at 45° C., and up to temperatures of 60° C. It also means that the performance obtained does not change or does not substantially change during the storage of the formulations.

In addition, they are very easy to rinse out.

One subject of the present invention is thus a dye composition comprising 12-hydroxystearic acid, one or more organic amines and one or more dyes chosen from oxidation dyes and direct dyes.

The invention also relates to a ready-to-use composition for the oxidation dyeing of keratin fibres and in particular of human keratin fibres such as the hair, comprising the extemporaneous mixing of a dye composition (A) according to the invention and of an oxidizing composition (B).

Another subject of the invention is a dyeing kit comprising, first, a dye composition (A) according to the invention, and, secondly, an oxidizing composition (B).

A subject of the invention is also a process for dyeing keratin fibres, especially human keratin fibres such as the hair, using said ready-to-use composition.

Other characteristics and advantages of the invention will emerge more clearly on reading the description and the examples that follow.

In the text hereinbelow, and unless otherwise indicated, the limits of a range of values are included within that range, especially in the expressions "between" and "ranging from . . . to . . . ".

Moreover, the expression "at least one" used in the present description is equivalent to the expression "one or more".

According to the invention, the dye composition comprises 12-hydroxystearic acid, one or more organic amines and one or more dyes chosen from oxidation dyes and direct dyes.

Preferably, 12-hydroxystearic acid is present in an amount ranging from 0.1% to 40% by weight, better still from 1% to 30% by weight and even better still from 5% to 25% by weight, relative to the total weight of the dye composition.

The organic amine(s) are preferably chosen from organic amines with a $pK_b$ at 25° C. of less than 12, preferably less than 10 and even more advantageously less than 6. It should be noted that it is the $pK_b$, corresponding to the function of highest basicity. In addition, the organic amines do not comprise any alkyl or alkenyl fatty chain comprising more than ten carbon atoms.

The organic amine(s) are chosen, for example, from alkanolamines, oxyethylenated and/or oxypropylenated ethylenediamines, amino acids and the compounds of formula (P) below:

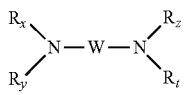 (P)

in which W is a divalent $C_1$ to $C_6$ alkylene group optionally substituted with one or more hydroxyl groups or a $C_1$ to $C_6$ alkyl group, and/or optionally interrupted with one or more heteroatoms such as O, or $NR_u$; $R_x$, $R_y$, $R_z$, $R_t$ and $R_u$, which may be identical or different, represent a hydrogen atom or a $C_1$ to $C_6$ alkyl, $C_1$ to $C_6$ hydroxyalkyl or $C_1$ to $C_6$ aminoalkyl group.

Examples of amines of formula (P) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$ to $C_8$ alkyl groups bearing one or more hydroxyl radicals.

Alkanolamines chosen from monoalkanolamines, dialkanolamines or trialkanolamines comprising from one to three identical or different $C_1$ to $C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-prop anediol, 3-amino-1,2-prop anediol, 3-dimethylamino-1,2-propanediol and tris(hydroxymethyl)aminomethane.

More particularly, the amino acids that may be used are of natural or synthetic origin, in their L, D or racemic form, and comprise at least one acid function chosen more particularly from carboxylic acid, sulfonic acid, phosphonic acid and phosphoric acid functions. The amino acids may be in neutral or ionic form.

As amino acids that may be used in the composition according to the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (Q) below, and also the salts thereof.

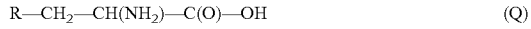 (Q)

in which R represents a group chosen from imidazolyl, preferably imidazolyl-4-yl; aminopropyl; aminoethyl; —$(CH_2)_2N(H)$—C(O)—$NH_2$; and —$(CH_2)_2$—N(H)—C(NH)—$NH_2$.

The compounds corresponding to formula (Q) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and balenine.

The organic amine may also be chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, n-amidinoalanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the organic amine(s) present in the dye composition according to the invention are chosen from alkanolamines, and amino acids in neutral or ionic form, in particular basic amino acids, and preferably corresponding to those of formula (Q) and guanidine carbonate.

More preferentially, the organic amine(s) present in the dye composition according to the invention are chosen from monoethanolamine (MEA), diethanolamine, triethanolamine, monoisopropanolamine, diisopropanolamine, 2-amino-2-methyl-1-propanol, 2-amino-2-methyl-1,3-propanediol, tris(hydroxymethylamino)methane, arginine, lysine, guanidine carbonate, and mixtures thereof.

The organic amine(s) are preferably present in an amount ranging from 0.1% to 20% by weight, preferably from 1% to 10% by weight and better still from 2% to 8% by weight, relative to the total weight of the dye composition.

As indicated previously, the dye composition according to the invention comprises one or more dyes chosen from oxidation dyes and direct dyes.

The oxidation dyes that may be used in the present invention are generally chosen from oxidation bases, optionally combined with one or more couplers.

The oxidation bases may be chosen especially from para-phenylenediamines, bis(phenyl)alkylenediamines, para-aminophenols, ortho-aminophenols and heterocyclic bases, and the addition salts thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, 2-hydroxypropyl-1,3-bis(N-hydroxyethyl)-p-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino- 5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, N,N-bis(β-hydroxyethyl)-para-phenylenediamine, 2-β-hydroxyethyl-para-phenylenediamine, 2-isopropyl-para-phenylenediamine, 2-hydroxypropyl-1,3-(bis-N- hydroxyethyl)-p-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane and the addition salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol and 5-acetamido-2-aminophenol, and the addition salts thereof.

Among the heterocyclic bases, examples that may be mentioned include pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl) ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-(2-hydroxyethoxy)-3-aminopyrazolo[1,5-a]pyridine, and 2-(4-methylpiperazinium-1-yl)-3-aminopyrazolo[1,5-a]pyridine chloride, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives, mention may be made of the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. Use may also be made of 4,5-diamino-1-(β-methoxyethyl)pyrazole.

Use will preferably be made of a 4,5-diaminopyrazole and even more preferentially of 4,5-diamino-1-(β-hydroxyethyl)pyrazole and/or a salt thereof.

Pyrazole derivatives that may also be mentioned include diamino-N,N-dihydropyrazolopyrazolones and in particular those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

Heterocyclic bases that will preferentially be used include 2-(2-hydroxyethoxy)-3-amino-pyrazolo[1,5-a]pyridine, 4,5-diamino-14(β-hydroxyethyl)pyrazole and 2,3-diamino-6,7-dihydro-1H,5H-pyrazolo[1,2-a]pyrazol-1-one and/or a salt thereof.

The couplers that may be used in the present invention may be chosen from those conventionally used for the dyeing of keratin fibres.

Among these couplers, mention may be made especially of meta-phenylenediamines, meta-aminophenols, meta-diphenols, naphthalene-based couplers and heterocyclic couplers, and also the addition salts thereof.

Examples that may be mentioned include 1,3-dihydroxybenzene, 1,3-dihydroxy-2-methylbenzene, 4-chloro-1,3-dihydroxybenzene, 1-hydroxy-3-aminobenzene, 1-methyl-2-hydroxy-4-β-hydroxyethylaminobenzene, 4-amino-2-hydroxytoluene, 5-amino-6-chloro-2-methylphenol, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl [3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the invention are in particular chosen from the addition salts with an acid, such as hydrochlorides, hydrobromides, sulfates, citrates, succinates, tartrates, lactates, tosylates, benzenesulfonates, phosphates and acetates.

The direct dye(s) may be chosen from synthetic direct dyes and natural direct dyes.

A direct dye is understood to be any dye which does not require the presence of a chemical oxidizing agent other than air for colouring.

A synthetic direct dye is understood to be any direct dye that does not exist in the natural state, including dyes obtained semi-synthetically.

Examples of suitable synthetic direct dyes that may be mentioned include azo, methine, carbonyl, azine, xanthene, nitro(hetero)aryl, tri(hetero)arylmethane, (metallo)porphyrin and phthalocyanine direct dyes, alone or as mixtures.

More particularly, the synthetic azo direct dyes include an —N═N— function in which the two nitrogen atoms are not simultaneously part of a ring. However, it is not excluded for one of the two nitrogen atoms of the sequence —N═N— to be part of a ring.

Examples of azo direct dyes that may be mentioned include the following dyes, described in Colour Index International, 3rd edition:

Disperse Red 17
Basic Red 22
Basic Red 76
Basic Yellow 57
Basic Brown 16
Basic Brown 17
Disperse Black 9.

The direct dyes of the methine family are more particularly compounds comprising at least one sequence chosen from >C═C< and —N═C< in which the two atoms are not simultaneously part of a ring. However, it is pointed out that one of the nitrogen or carbon atoms of the sequences may be part of a ring.

More particularly, the methine dyes are derived from methine, azomethine, hydrazono, mono- and diarylmethane, indoamine (or diphenylamine), indophenol, indoaniline and (hemi)cyanine compounds, such as styryl, streptocyanine, carbocyanine, azacarbocyanine, diazacarbocyanine and tetraazacarbocyanine, such as tetraazapentamethine, dyes, and the optical and geometric isomers thereof.

Among the azo, azomethine, methine or tetraazapentamethine direct dyes that may be used according to the invention, mention may be made of the cationic dyes described in patent applications WO 95/15144, WO 95/01772 and EP 714954; FR 2189006, FR 2285851, FR 2140205, EP 1378544, EP 1674073.

Among the indoamine dyes that may be used according to the invention, mention may be made of the following compounds:

2-β-hydroxyethlyamino-5-[bis(β-4'-hydroxyethyl)amino]anilino-1,4-benzoquinone;

2-β-hydroxyethylamino-5-(2'-methoxy-4'-amino)anilino-1,4-benzoquinone;

3-N-(2'-chloro -4'-hydroxy)phenylacetylamino-6-methoxy-1,4-benzoquinone imine;

3-N-(3'-chloro-4'-methylamino)phenylureido-6-methyl-1,4-benzoquinone imine; and

3-[4'-N-(ethyl,carbamylmethyl)amino]phenylureido-6-methyl-1,4-benzoquinone imine.

Among the tetraazapentamethine dyes that may be used according to the invention, mention may be made of the following compounds appearing in the table below:

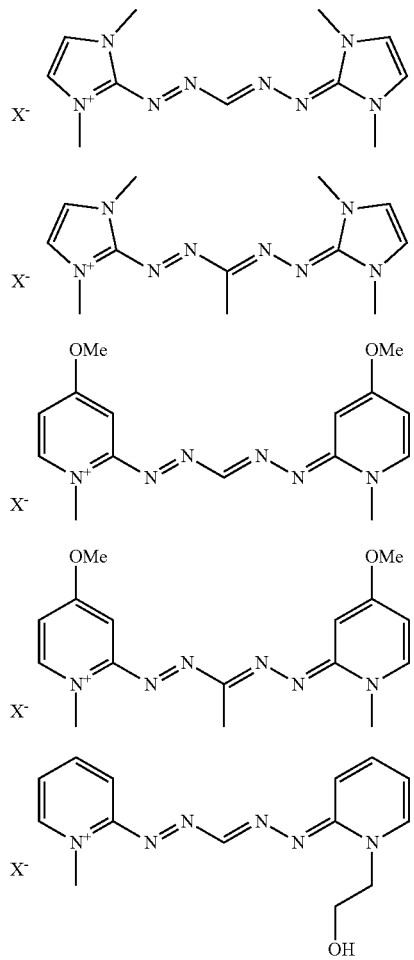

-continued

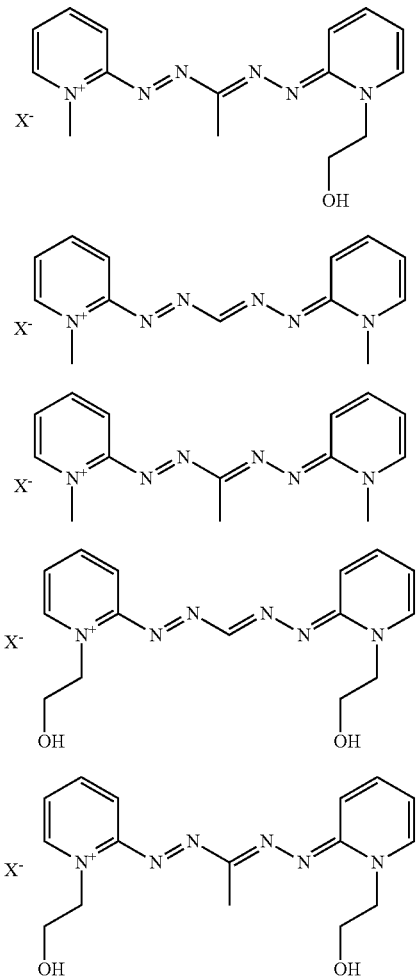

X⁻ representing an anion preferably chosen from chloride, iodide, methyl sulfate, ethyl sulfate, acetate and perchlorate.

As regards the synthetic direct dyes of the carbonyl family, examples that may be mentioned include dyes chosen from quinone, acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin dyes.

Among the quinone direct dyes, mention may be made of the following dyes:
Disperse Red 15
Solvent Violet 13
Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99
and also the following compounds:
1-N-methylmorpholiniumpropylamino-4-hydroxyanthraquinone;
1-aminopropylamino-4-methylaminoanthraquinone;
1-aminopropylaminoanthraquinone;
5-β-hydroxyethyl-1,4-diaminoanthraquinone;
2-aminoethylaminoanthraquinone;
1,4-bis(β,γ-dihydroxypropylamino)anthraquinone.

As regards the synthetic direct dyes of the azine family, mention may be made in particular of azine, fluorindine, acridine, (di)oxazine and (di)thiazine dyes.

Examples of azine dyes that may be mentioned include the following compounds:
Basic Blue 17
Basic Red 2.

As regards the synthetic direct dyes of the xanthene family, mention may be made in particular of xanthene, thioxanthene and pyronine dyes.

The nitro(hetero)aryl synthetic direct dyes are more particularly nitrobenzene or nitropyridine direct dyes.

Among the nitrobenzene direct dyes that may be used according to the invention, mention may be made in a nonlimiting manner of the following compounds:
1,4-diamino-2-nitrobenzene;
1-amino-2 nitro-4-β-hydroxyethylaminobenzene;
1-amino-2 nitro-4-bis(β-hydroxyethyl)aminobenzene;
1,4-bis(β-hydroxyethylamino)-2-nitrobenzene;
1-β-hydroxyethylamino-2-nitro-4-bis(β-hydroxyethylamino)benzene;
1-β-hydroxyethylamino-2-nitro-4-aminobenzene;
1-β-hydroxyethylamino-2-nitro-4-(ethyl)(β-hydroxyethyl)aminobenzene;
1-amino-3-methyl-4-β-hydroxyethylamino-6-nitrobenzene;
1-amino-2-nitro-4-β-hydroxyethylamino-5-chlorobenzene;
1,2-diamino-4-nitrobenzene;
1-amino-2-β-hydroxyethylamino-5-nitrobenzene;
1,2-bis(β-hydroxyethylamino)-4-nitrobenzene;
1-amino-2-tris(hydroxymethyl)methylamino-5-nitrobenzene;
1-hydroxy-2-amino-5-nitrobenzene;
1-hydroxy-2-amino-4-nitrobenzene;
1-hydroxy-3-nitro-4-aminobenzene;
1-hydroxy-2-amino-4,6-dinitrobenzene;
1-β-hydroxyethyloxy-2-β-hydroxyethylamino-5-nitrobenzene;
1-methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-I3,γ-dihydroxypropyloxy-2-nitrobenzene;
1-β,γ-dihydroxypropylamino-4-trifluoromethyl-2-nitrobenzene;
1-β-hydroxyethylamino-4-trifluoromethyl-2-nitrobenzene;
1-β-hydroxyethylamino-3-methyl-2-nitrobenzene;

1-β-aminoethylamino-5-methoxy-2-nitrobenzene;
1-hydroxy-2-chloro-6-ethylamino-4-nitrobenzene;
1-hydroxy-2-chloro-6-amino-4-nitrobenzene;
1-hydroxy-6-bis(β-hydroxyethyl)amino-3-nitrobenzene;
1-β-hydroxyethylamino-2-nitrobenzene;
1-hydroxy-4-β-hydroxyethylamino-3-nitrobenzene.

Among the triarylmethane dyes that can be used according to the invention, mention may be made of the following compounds:

Basic Green 1
Basic Violet 3
Basic Violet 14
Basic Blue 7
Basic Blue 26.

As regards the (metallo)porphyrin or phthalocyanine synthetic direct dyes, use may be made of cationic or non-cationic compounds, optionally comprising one or more metals or metal ions, for instance alkali metals and alkaline-earth metals, zinc and silicon.

Examples of particularly suitable synthetic direct dyes that may be mentioned include nitrobenzene dyes; azo, methine, azomethine, hydrazono or styryl direct dyes; azacarbocyanines such as tetraazacarbocyanines (tetraazapentamethines); quinone direct dyes, and in particular anthraquinone, naphthoquinone or benzoquinone direct dyes; azine direct dyes; xanthene direct dyes; triarylmethane direct dyes; indoamine direct dyes, indigoid direct dyes, phthalocyanine direct dyes and porphyrin direct dyes, alone or as mixtures.

These dyes may be monochromophoric dyes (i.e. dyes comprising only one dye) or polychromophoric, preferably dichromophoric or trichromophoric, dyes; the chromophores may be identical or different, and from the same chemical family or otherwise. It should be noted that a polychromophoric dye comprises a plurality of groups each derived from a molecule that absorbs in the visible region between 400 and 800 nm. Furthermore, this absorbance of the dye does not require any prior oxidation thereof, or combination with one or more other chemical species.

In the case of polychromophoric dyes, the chromophores are connected together by means of at least one linker L, which may be cationic or non-cationic.

The linker L is preferably a linear, branched or cyclic $C_1$-$C_{20}$ alkyl chain which is optionally interrupted and/or terminated with at least i) a heteroatom (such as nitrogen N(R), N$^+$R, R', Q$^-$, oxygen or sulfur), ii) a group C(O), C(S), S(O) or S(O)$_2$ or iii) a combination thereof, optionally interrupted with at least one heterocycle which may or may not be fused to a phenyl nucleus, and which comprises at least one quaternized nitrogen atom forming part of said ring system, and optionally at least one other heteroatom (such as oxygen, nitrogen or sulfur), optionally interrupted with at least one substituted or unsubstituted phenyl or naphthyl group, optionally at least one quaternary ammonium group substituted with two $C_1$-$C_{15}$ alkyl groups which are optionally substituted; the linker does not contain a nitro, nitroso or peroxo group, and R and R', which may be identical or different, represent a hydrogen atom or a $C_1$-$C_6$ alkyl group which is optionally substituted, preferably with at least one hydroxyl group, and Q$^-$ represents an organic or mineral anionic counterion such as a halide or an alkyl sulfate.

If the heterocycles or aromatic nuclei are substituted, they are substituted, for example, with one or more $C_1$-$C_8$ alkyl groups optionally substituted with a hydroxyl, $C_1$-$C_2$ alkoxy, $C_2$-$C_4$ hydroxyalkoxy, acetylamino or amino group substituted with one or two $C_1$-$C_4$ alkyl groups, optionally bearing at least one hydroxyl group, or the two groups possibly forming, with the nitrogen atom to which they are attached, a 5- or 6-membered heterocycle, optionally comprising another nitrogen or non-nitrogen heteroatom; a halogen atom; a hydroxyl group; a $C_1$-$C_2$ alkoxy group; a $C_2$-$C_4$ hydroxyalkoxy group; an amino group; an amino group substituted with one or two identical or different $C_1$-$C_4$ alkyl groups, optionally bearing at least one hydroxyl group.

According to one particularly advantageous embodiment of the invention, the dye(s) are chosen from (poly)azo dyes such as (di)azo dyes; hydrazono dyes; (poly)methine dyes such as styryl dyes; anthraquinone dyes or naphthalimide dyes. Preferably, these dyes are (poly)cationic.

According to an even more preferred embodiment of the invention, the dyes are chosen from cationic dyes known as "basic dyes".

Mention may be made of the cationic hydrazono dyes of formulae (I) and (I'), the azo dyes (II) and (II') and the diazo dyes (III) below:

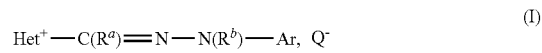

(I)

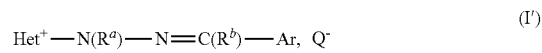

(I')

(II)

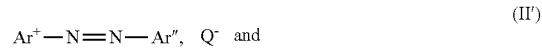

(II')

(III)

in which formulae (I), (I'), (II), (II') and (III):

Het$^+$ represents a cationic heteroaryl group, preferably bearing an endocyclic cationic charge, such as imidazolium, indolium or pyridinium, optionally substituted with one or more $C_1$-$C_8$ alkyl groups such as methyl;

Ar$^+$ represents an aryl group, such as phenyl or naphthyl, bearing an exocyclic cationic charge, preferentially ammonium, particularly tri($C_1$-$C_8$ alkyl)ammonium such as trimethylammonium;

Ar represents an aryl group, in particular phenyl, which is optionally substituted, preferably with one or more electron-donating groups such as i) optionally substituted $C_1$-$C_8$ alkyl, ii) optionally substituted $C_1$-$C_8$ alkoxy, iii) (di)($C_1$-$C_8$ alkyl)amino optionally substituted on the alkyl group(s) with a hydroxyl group, iv) aryl($C_1$-$C_8$ alkyl)amino, or v) optionally substituted N—($C_1$-$C_8$ alkyl)-N-aryl($C_1$-$C_8$ alkyl)amino, or alternatively Ar represents a julolidine group;

Ar' is an optionally substituted divalent (hetero)arylene group such as phenylene, particularly para-phenylene, or naphthalene, which are optionally substituted, preferably with one or more $C_1$-$C_8$ alkyl, hydroxyl or $C_1$-$C_8$ alkoxy groups;

Ar" is an optionally substituted (hetero)aryl group such as phenyl or pyrazolyl, which are optionally substituted, preferably with one or more $C_1$-$C_8$ alkyl, hydroxyl, (di)($C_1$-$C_8$ alkyl)amino, $C_1$-$C_8$ alkoxy or phenyl groups;

$R^a$ and $R^b$, which may be identical or different, represent a hydrogen atom or a $C_1$-$C_8$ alkyl group, which is optionally substituted, preferentially with a hydroxyl group; or alternatively the substituent $R^a$ with a substituent of Het$^+$ and/or $R^b$ with a substituent of Ar form, together with the atoms that bear them, a (hetero)cycloalkyl;

particularly, $R^a$ and $R^b$ represent a hydrogen atom or a $C_1$-$C_4$ alkyl group, which is optionally substituted with a hydroxyl group;

$Q^-$ represents an organic or mineral anionic counterion, such as a halide or an alkyl sulfate.

In particular, the dyes of the invention are cationically charged, endocyclic, azo and hydrazono dyes of formulae (I), (I') and (II) as defined previously. The dyes of formulae (I), (I') and (II) described in patent applications WO 95/15144, WO 95/01772 and EP 714954 are more particularly preferred.

Dyes of the invention are preferably chosen from the following compounds:

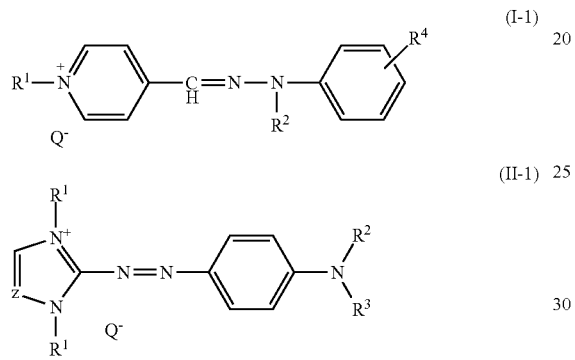

in which formulae (I-1) and (II-1):

R' represents a $C_1$-$C_4$ alkyl group such as methyl;

$R^2$ and $R^3$, which may be identical or different, represent a hydrogen atom or a $C_1$-$C_4$ alkyl group such as methyl; and $R^4$ represents a hydrogen atom or an electron-donating group such as optionally substituted $C_1$-$C_8$ alkyl, optionally substituted $C_1$-$C_8$ alkoxy, or (di)($C_1$-$C_8$ alkyl)amino optionally substituted on the alkyl group(s) with a hydroxyl group; particularly, $R^4$ is a hydrogen atom;

Z represents a CH group or a nitrogen atom, preferentially CH;

$Q^-$ is as defined previously.

In particular, the dyes of formulae (I-1) and (II-1) are chosen from Basic Red 51, Basic Yellow 87 and Basic Orange 31 or their derivatives:

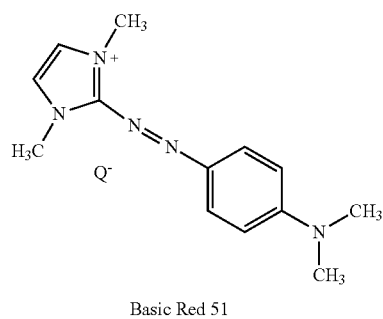

Basic Red 51

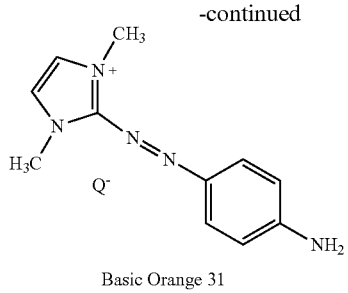

Basic Orange 31

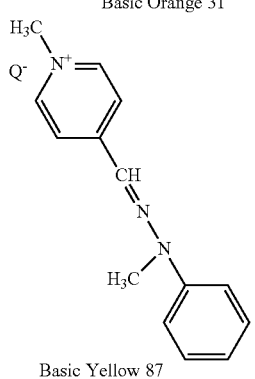

Basic Yellow 87 where $Q^-$ is as defined previously, and represents in particular a halide such as a chloride, or an alkyl sulfate such as methyl sulfate or mesityl.

Mention may also be made of 1-(4'-aminodiphenylazo)-2-methyl-4-bis(β-hydroxyethyl)aminobenzene.

Among the polychromophoric dyes, mention may be made more particularly of the symmetrical or non-symmetrical di- or trichromophoric azo and/or azomethine (hydrazone) dyes, comprising on the one hand at least one 5- or 6-membered aromatic heterocycle, optionally fused, which comprises at least one quaternized nitrogen atom forming part of said heterocycle, and optionally at least one other heteroatom (such as nitrogen, sulfur or oxygen), and, on the other hand, at least one optionally substituted phenyl or naphthyl group optionally bearing at least one group OR in which R represents a hydrogen atom, an optionally substituted $C_1$-$C_6$ alkyl group, an optionally substituted phenyl nucleus, or at least one group N(R')$_2$ with R', which may be identical or different, representing a hydrogen atom, an optionally substituted $C_1$-$C_6$ alkyl group or an optionally substituted phenyl nucleus; the groups R' possibly forming, with the nitrogen atom to which they are attached, a saturated 5- or 6-membered heterocycle, or else one and/or both of the groups R' may each form a saturated 5- or 6-membered heterocycle with the carbon atom of the aromatic ring that is ortho to the nitrogen atom.

Aromatic cationic heterocycles that may preferably be mentioned include 5- or 6-membered rings containing 1 to 3 nitrogen atoms and preferably 1 or 2 nitrogen atoms, one being quaternized; said heterocycle moreover being optionally fused to a benzene nucleus. It should similarly be noted that the heterocycle may optionally comprise another heteroatom other than nitrogen, for instance sulfur or oxygen.

If the heterocycles or phenyl or naphthyl groups are substituted, they are substituted, for example, with one or more $C_1$-$C_8$ alkyl groups optionally substituted with a hydroxyl, $C_1$-$C_2$ alkoxy, $C_2$-$C_4$ hydroxyalkoxy, acetylamino or amino group substituted with one or two $C_1$-$C_4$ alkyl groups, optionally bearing at least one hydroxyl group, or the two groups possibly forming, with the nitrogen atom to which they are attached, a 5- or 6-membered heterocycle, optionally comprising another nitrogen or non-nitrogen heteroatom; a halogen atom; a hydroxyl group; a $C_1$-$C_2$ alkoxy group; a $C_2$-$C_4$ hydroxyalkoxy group; an amino group; an amino group substituted with one or two identical or different $C_1$-$C_4$ alkyl groups, optionally bearing at least one hydroxyl group.

These polychromophores are connected together via at least one linker L as defined previously.

The bonding between the linker L and each chromophore generally takes place via a heteroatom substituent on the phenyl or naphthyl nucleus or via the quaternized nitrogen atom of the cationic heterocycle.

The dye may comprise identical or different chromophores.

As examples of such dyes, reference may be made in particular to patent applications EP 1 637 566, EP 1 619 221, EP 1 634 926, EP 1 619 220, EP 1 672 033, EP 1 671 954, EP 1 671 955, EP 1 679 312, EP 1 671 951, EP 167 952, EP 167 971, WO 06/063 866, WO 06/063 867, WO 06/063 868, WO 06/063 869, EP 1 408 919, EP 1 377 264, EP 1 377 262, EP 1 377 261, EP 1 377 263, EP 1 399 425, EP 1 399 117, EP 1 416 909, EP 1 399 116 and EP 1 671 560.

It is equally also possible to use cationic synthetic direct dyes which are mentioned in the following patent applications: EP 1 006 153, which describes dyes comprising two chromophores of anthraquinone type connected via a cationic linker; EP 1 433 472, EP 1 433 474, EP 1 433 471 and EP 1 433 473, which describe identical or different dichromophoric dyes, connected via a cationic or non-cationic linker, and also EP 6 291 333, which in particular describes dyes comprising three chromophores, one of them being an anthraquinone chromophore, to which are attached two chromophores of azo or diazacarbocyanine type or an isomer thereof.

The term "natural dyes" means any dye or dye precursor that is naturally occurring and that is produced either by extraction (and possibly purification) from a plant or animal matrix, optionally in the presence of natural compounds such as ash or ammonia, or by chemical synthesis.

Natural dyes that may be mentioned include lawsone, henna, curcumin, chlorophyllin, alizarin, kermesic acid, purpurin, purpurogallin, indigo, Tyrian purple, sorghum, carminic acid, catechin, epicatechin, juglone, bixin, betanin, quercetin, chromene dyes and chroman dyes, including haematein and brazilein, and laccaic acids.

Preferably, the natural dyes used in the invention are chosen from curcumin, chlorophyllin, chromene dyes, chroman dyes and laccaic acids.

According to the invention, the terms "chromene dye" and "chroman dye" mean dyes which comprise in their structure at least one bicycle of formula (IV) below:

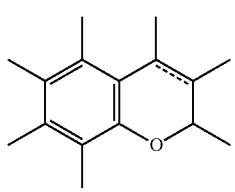

IV the endocyclic ⎓ bond representing a carbon-carbon single bond or a carbon-carbon double bond, as illustrated by formula IV-1 denoting the chromene family and formula IV-2 denoting the chroman family below:

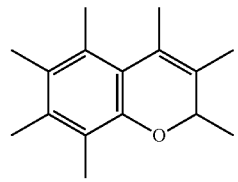

IV-1

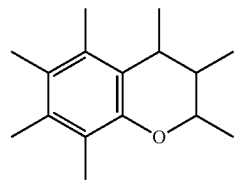

IV-2

More particularly, the dyes having in their structure a bicycle of formula (IV) are chosen from the dyes having the following formulae:

formula (V), comprising in its structure the bicycle of formula IV-2,

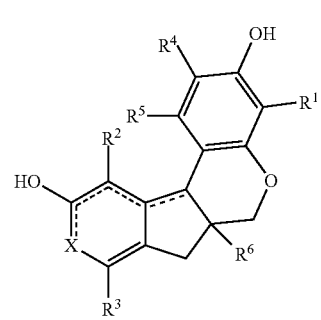

(V)

in which:

i) ⎓ represents a carbon-carbon single bond or a carbon-carbon double bond, the sequence of these ⎓ bonds denoting two carbon-carbon single bonds and two carbon-carbon double bonds, said bonds being conjugated, ii) X represents a group:

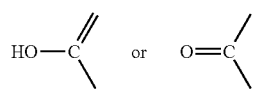

iii) $R^1$, $R^2$, $R^3$, $R^4$, $R^5$ and $R^6$, which may be identical or different, represent, independently of each other, a hydrogen atom, a hydroxyl group, an optionally substituted alkyl group, an optionally substituted alkoxy group or an optionally substituted acyloxy group, and also the tautomeric and/or mesomeric forms thereof, the stereoisomers thereof, the addition salts thereof with a cosmetically acceptable acid or base, and the hydrates thereof, and formula (VI), comprising in its structure the bicycle of formula IV-1,

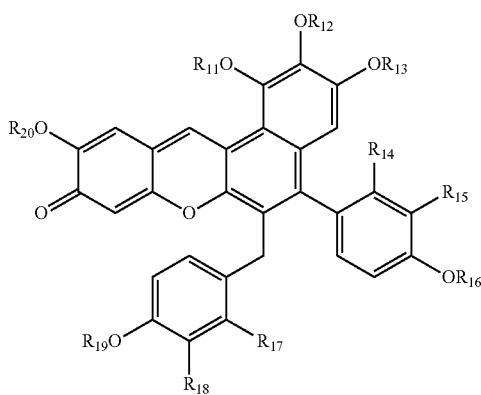

(VI)

in which:

$R^{11}$, $R^{12}$, $R^{13}$, $R^{16}$, $R^{19}$ and $R^{20}$, which may be identical or different, represent, independently of each other, a hydrogen atom or a $C_1$-$C_4$ alkyl group, $R^{14}$, $R^{15}$, $R^{17}$ and $R^{18}$, which may be identical or different, represent, independently of each other, a hydrogen atom, a hydroxyl group or a $C_1$-$C_4$ alkoxy group, and also the tautomeric and/or mesomeric forms thereof, the stereoisomers thereof, the addition salts thereof with a cosmetically acceptable acid or base, and the hydrates thereof.

As regards the dyes of formula (V) as defined previously, they may be in two tautomeric forms noted (Va) and (Vb):

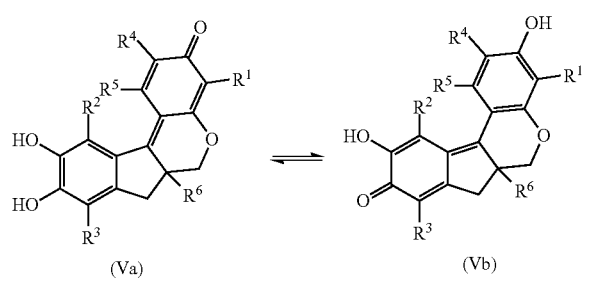

(Va)                  (Vb)

The alkyl groups mentioned in the preceding definitions of the substituents are linear or branched, saturated, generally $C_1$-$C_{20}$, particularly $C_1$-$C_{10}$ and preferably $C_1$-$C_6$ hydrocarbon-based groups, such as methyl, ethyl, propyl, butyl, pentyl and hexyl.

The alkoxy groups are alkyl-oxy groups with alkyl groups as defined previously and preferably the alkoxy groups are $C_1$-$C_{10}$, such as methoxy, ethoxy, propoxy and butoxy.

The alkyl or alkoxy groups, when they are substituted, may be substituted with at least one substituent borne by at least one carbon atom, chosen from:

a halogen atom;
a hydroxyl group;
a $C_1$-$C_2$ alkoxy group;
a $C_1$-$C_{10}$ alkoxycarbonyl group;
a $C_2$-$C_4$ (poly)hydroxyalkoxy group;
an amino group;
a 5- or 6-membered heterocycloalkyl group;
an optionally cationic 5- or 6-membered heteroaryl group, preferentially imidazolium, optionally substituted with a $(C_1$-$C_4)$alkyl group, preferentially methyl;

an amino group substituted with one or two identical or different $C_1$-$C_6$ alkyl groups, optionally bearing at least:
one hydroxyl group;

an amino group optionally substituted with one or two optionally substituted $C_1$-$C_3$ alkyl groups, it being possible for said alkyl groups to form, with the nitrogen atom to which they are attached, a saturated or unsaturated and optionally substituted 5- to 7-membered heterocycle, optionally comprising at least one other nitrogen or non-nitrogen heteroatom, a quaternary ammonium group —$N^+R'R''R'''$, $M^-$ for which R', R'' and R''', which may be identical or different, represent a hydrogen atom or a $C_1$-$C_4$ alkyl group; and $M^-$ represents the counterion of the corresponding organic or mineral acid or of the corresponding halide;

or an optionally cationic 5- or 6-membered heteroaryl group, preferentially imidazolium, optionally substituted with a $(C_1$-$C_4)$ alkyl group, preferentially methyl;

an acylamino group (—NR—COR') in which the group R is a hydrogen atom or a $C_1$-$C_4$ alkyl group optionally bearing at least one hydroxyl group and the group R' is a $C_1$-$C_2$ alkyl group;

a carbamoyl group $((R)_2N$—CO—) in which the groups R, which may be identical or different, represent a hydrogen atom or a $C_1$-$C_4$ alkyl group optionally bearing at least one hydroxyl group;

an alkylsulfonylamino group ($R'SO_2$—NR—) in which the group R represents a hydrogen atom or a $C_1$-$C_4$ alkyl group optionally bearing at least one hydroxyl group and the group R' represents a $C_1$-$C_4$ alkyl group, or a phenyl group;

an aminosulfonyl group $((R)_2N$—$SO_2$—) in which the groups R, which may be identical or different, represent a hydrogen atom or a $C1$-$C_4$ alkyl group optionally bearing at least one hydroxyl group;

a carboxylic group in acid or salified form (preferably with an alkali metal or a substituted or unsubstituted ammonium);

a cyano group;
a nitro group;
a carboxyl or glycosylcarbonyl group;
a phenylcarbonyloxy group optionally substituted with one or more hydroxyl groups;
a glycosyloxy group; and
a phenyl group optionally substituted with one or more hydroxyl groups. The term "glycosyl group" means a group originating from a mono- or polysaccharide.

Preferably, the alkyl or alkoxy groups of formula (V) are unsubstituted.

According to one particular embodiment of the invention, the dyes of formula (V) comprise a group $R^6$ which represents a hydroxyl group.

In one preferred variant, X represents a group O=C.

Another particular embodiment of the invention relates to the dyes of formula (V), for which the group $R^1$ represents a hydrogen atom or a hydroxyl group.

More particularly, the dyes of formula (V) are chosen from haematein and brazilein.

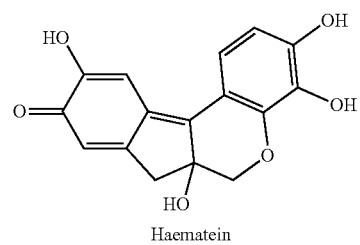

Haematein

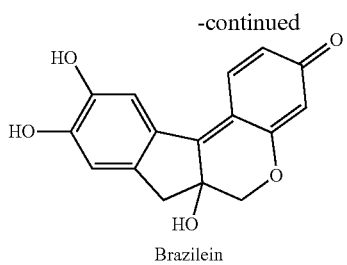

Brazilein

Brazilein is a conjugated form of a chroman compound of formula IV-2. The tautomeric structures (Va) and (Vb) illustrated above are found in the scheme below.

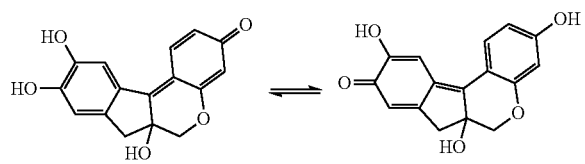 [SMILES: O=C1C=CC2=C3c4cc(O)c(O)cc4CC3(O)COC2=C1 ; O=C1C=C2CC3(O)COc4cc(O)ccc4C3=C2C=C1O]

Brazilein and haematein or the haematoxylin/haematein and brazilin/brazilein pairings may be obtained synthetically or by extraction of plants known to be rich in these dyes.

The dyes of formula (V) may be used in the form of extracts. Use may be made of the following plant extracts (genus and species): *Haematoxylon campechianum, Haematoxylon brasiletto, Caesalpinia echinata, Caesalpinia sappan, Caesalpinia spinosa* and *Caesalpinia brasiliensis*.

The extracts are obtained by extraction of various plant parts, such as, for example, the root, wood, bark or leaves.

According to a particular embodiment of the invention, the natural dyes of formula (V) are obtained from logwood, pernambuco wood, sappan wood and Brazil wood.

The salts of the dyes of formulae (V) and (VI) of the invention may be salts of cosmetically acceptable acids or bases.

The acids may be mineral or organic. Preferably, the acid is hydrochloric acid, which results in chlorides.

The bases may be mineral or organic. In particular, the bases are alkaline hydroxides, such as sodium hydroxide, resulting in sodium salts.

Preferably, the dye(s) of formulae (V) and (VI) included in the composition according to the invention are derived from plant extracts. Use may also be made of mixtures of plant extracts.

The natural extracts of the dyes according to the invention may be in the form of powders or liquids. Preferably, the extracts are in powder form.

In another variant of the invention, the natural dyes are chosen from laccaic acids.

For the purposes of the present invention, the term "laccaic acid" means a compound having in its structure a unit of the type:

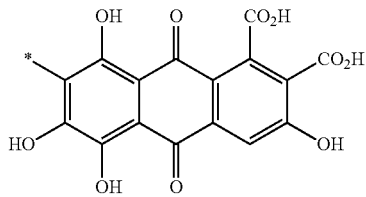 [SMILES: *c1c(O)c(O)c2c(c1O)C(=O)c1c(cc(O)c(C(=O)O)c1C(=O)O)C2=O]

Preferably, the laccaic acids of the invention are of formula (VII) below:

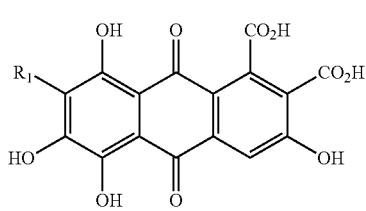

with $R_1$ denoting a phenyl group substituted with at least one hydroxyl group, and preferably with a hydroxyl group that is advantageously in the ortho position relative to the bond attaching it to the fused nuclei.

In particular, the phenyl group $R_1$ comprises, besides a hydroxyl group, at least one group —$CH_2R_2$, $R_2$ denoting an acetamidomethyl ($CH_3CONHCH_2$—), hydroxymethyl ($HOCH_2$—) or 2-aminoacetic acid ($HO_2C(NH_2)CH$—) group.

Preferentially, the laccaic acids of the invention are chosen from laccaic acids A, B, C and D, or mixtures thereof, and more particularly chosen from A, B and C, or mixtures thereof.

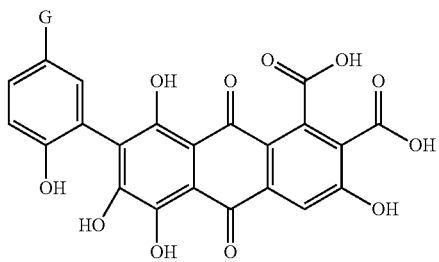

Laccaic acid A G: —$CH_2CH_2NHC(O)CH_3$
Laccaic acid B G: —$CH_2CH_2OH$
Laccaic acid C G: —$CH_2CH(NH_2)C(O)OH$
Laccaic acid D G: —$CH_2CH_2NH_2$ Laccaic Acids A, B, C and D A laccaic acid according to the invention that may in particular be used is the dye CI Natural Red 25, CI 75450, CAS-60687-93-6, which is often referred to as laccaic acid. This is a dye of natural origin originating from the secretions of an insect, *Coccus laccae* (Lacifer Lacca Kerr), which is generally found on the twigs of certain trees native to South-East Asia.

CI Natural Red 25 generally contains two major constituents in its composition: laccaic acid A and laccaic acid B. It may also contain a small amount of laccaic acid C.

Needless to say, use may also be made of the purified forms of the laccaic acids of formula (VII).

Even more preferentially, the natural direct dyes are chosen from haematein and brazilein.

Preferably, the dye(s) are one or more oxidation dyes optionally combined with one or more direct dyes.

Better still, the dye(s) are chosen from para-phenylenediamines, para-aminophenols, pyrazole derivatives, meta-phenylenediamines, meta-aminophenols, meta-diphenols, and mixtures thereof, and more particularly from para-phenylenediamine, para-tolylenediamine, N,N-bis(β-hydroxyethyl)-para-phenylenediamine, 2-hydroxypropyl-1,3-(bis-N- hydroxyethyl)-p-phenylenediamine, p-aminophenol, 3-methyl-p-aminophenol, 2-(2-hydroxyethoxy)-3-aminopyrazolo[1,5-a]pyridine, 4,5-diamino-1-(β-hydroxyethyl)pyrazole, 2,3-diamino-6,7- dihydro -1H,5H-pyrazolo[1,2-a]pyrazol-1-one, 1,3-dihydroxybenzene, 2-methyl-1,3-dihydroxybenzene, 4-chloro-1,3-dihydroxybenzene, 1-hydroxy-3-aminobenzene, 1-methyl-2-hydroxy-4-beta-hydroxyethylaminobenzene, 2-methyl-5-aminophenol, 5-amino-6-chloro-2-methylphenol and 2,4-diamino-1-(β-hydroxyethyloxy)benzene, the addition salts thereof and mixtures thereof.

The dye(s) may each represent from 0.0001% to 20% by weight, preferably from 0.001% to 15% by weight and better still from 0.01% to 10% by weight relative to the total weight of the dye composition.

The dye composition is preferably aqueous. More particularly, it comprises an amount of water preferably ranging from 20% to 95% by weight, better still from 40% to 90% by weight and even better still from 55% to 85% by weight relative to the total weight thereof.

The dye composition according to the invention may also comprise one or more alkaline agents other than organic amines.

It may be mineral or organic.

More particularly, the alkaline agent(s) other than organic amines may be chosen from:
 a) aqueous ammonia,
 b) mineral or organic hydroxides,
 c) alkali metal silicates, such as sodium metasilicates, and
 d) carbonates and bicarbonates particularly of an alkali metal or alkaline-earth metal, such as sodium carbonate or bicarbonate and potassium carbonate or bicarbonate.

The mineral or organic hydroxides are preferably chosen from hydroxides of an alkali metal, hydroxides of an alkaline-earth metal, for instance sodium hydroxide or potassium hydroxide, hydroxides of a transition metal, such as hydroxides of metals from Groups III, IV, V and VI of the Periodic Table of the Elements, hydroxides of lanthanides or actinides, and quaternary ammonium hydroxides.

The preferred alkaline agents other than organic amines are in particular aqueous ammonia, sodium or potassium hydroxide, sodium or potassium carbonate, sodium or potassium bicarbonate, and mixtures thereof.

When the composition according to the invention comprises one or more alkaline agent(s) other than organic amines, they are present in an amount preferably ranging from 0.01% to 30% by weight, better still from 0.1% to 20% by weight and even better still from 1% to 10% by weight, relative to the total weight of the dye composition.

The organic amine(s) and the different alkaline agent(s) are introduced in a content such that the pH of the composition according to the invention is advantageously between 8 and 12 and better still between 9 and 11.

The composition according to the present invention may optionally also comprise one or more organic solvents.

Examples of organic solvents that may be mentioned include linear or branched $C_2$ to $C_4$ alkanols, such as ethanol and isopropanol; glycerol; polyols and polyol ethers, for instance 2-butoxyethanol, propylene glycol, hexylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The content of the organic solvent(s), when they are present in the composition, preferably ranges from 0.01% to 30% by weight and more preferentially from 2% to 25% by weight, relative to the total weight of the composition.

The composition according to the present invention may also optionally comprise one or more additives, different from the compounds of the invention, and among which mention may be made of fatty substances, cationic, anionic, nonionic or amphoteric polymers or mixtures thereof, anti-dandruff agents, anti-seborrhoea agents, agents for preventing hair loss and/or for promoting hair regrowth, vitamins and provitamins including panthenol, sunscreens, mineral or organic pigments, sequestrants, plasticizers, solubilizers, acidifying agents, mineral or organic thickeners, especially polymeric thickeners, opacifiers or nacreous agents, antioxidants, hydroxy acids, fragrances, preserving agents, pigments and ceramides.

Needless to say, a person skilled in the art will take care to select this or these optional additional compound(s) such that the advantageous properties intrinsically associated with the composition in accordance with the invention are not, or are not substantially, adversely affected by the envisaged addition(s).

The above additives may generally be present in an amount comprised, for each of them, of between 0 and 20% by weight relative to the total weight of the dye composition according to the invention.

The invention also relates to a process for preparing the dye composition as defined above, comprising:
 the mixing of 12-hydroxystearic acid, one or more organic amines and one or more dyes,
 optionally heating, for example for 1 to 10 minutes at a temperature ranging from 60 to 70° C., or for 30 minutes to 2 hours, at a temperature ranging from 20° C. to 40° C., with or without stirring, preferably with gentle stirring, and
 cooling of the mixture, preferably without stirring, to room temperature (18-25° C.).

Yet another subject is a ready-to-use composition which results from the extemporaneous mixing of a dye composition (A) as described above and of an oxidizing composition (B).

Compositions (A) and (B) are preferably mixed in an (A)/(B) weight ratio ranging from 0.1 to 5, better still from 0.2 to 2.

The oxidizing composition (B) comprises one or more oxidizing agents.

The oxidizing agent used in the context of the invention is a chemical oxidizing agent other than atmospheric oxygen.

Said oxidizing agent(s) are preferably chosen from the group consisting of hydrogen peroxide, urea peroxide, alkali metal bromides or ferricyanides, peroxygenated salts, for instance persulfates, perborates, peracids and precursors thereof, and alkali metal or alkaline-earth metal percarbonates.

Most particularly, the oxidizing agent is hydrogen peroxide.

The oxidizing agent(s) may represent from 0.1% to 20% by weight, preferably from 0.5% to 15% by weight and better still from 2% to 12% by weight, relative to the total weight of the oxidizing composition (B).

A subject of the present invention is also a process for dyeing keratin fibres, and in particular human keratin fibres such as the hair, which consists in applying to said fibres a composition as described previously, and in particular a ready-to-use composition as defined previously, resulting from the extemporaneous mixing of a dye composition (A) as described above and of an oxidizing composition (B) as described above.

In particular, the composition of the invention or the ready-to-use composition of the invention is applied to wet or dry keratin fibres.

The composition is advantageously left to stand on the keratin fibres for a time ranging from 1 minute to 1 hour and more preferentially for a time ranging from 5 to 45 minutes.

On the conclusion of the dyeing process, the keratin fibres are advantageously rinsed with water. They may optionally be washed with a shampoo, followed by rinsing with water, before being dried or left to dry.

Another subject of the invention concerns a multi-compartment device, or a kit for dyeing keratin fibres, comprising at least two compartments:

a first compartment containing a dye composition (A) as described above; and a second compartment containing an oxidizing composition (B) as described above.

According to one variant of the invention, the kit also comprises an additional compartment containing an additional composition comprising one or more treating agents.

The compositions of the kit are packaged in separate compartments, which may be optionally accompanied by suitable identical or different application means, such as fine brushes, coarse brushes or sponges.

The examples that follow are given purely as illustrations of the present invention.

EXAMPLES

Example 1:

The dye composition A according to the invention and a comparative composition B are prepared using the ingredients indicated in the following tables. The amounts indicated are expressed as weight percentages of active material relative to the total weight of the dye composition.

| Composition | A (invention) |
|---|---|
| Ammonium hydroxide | 2 |
| Powdered sodium metabisulfite | 0.7 |
| Monoethanolamine | 3 |
| Ethylenediaminetetraacetic acid | 0.2 |
| Guanidine carbonate | 0.8 |
| 1-β-Hydroxyethyloxy-2,4-diaminobenzene dihydrochloride | 0.013 |
| N,N-Bis(2-hydroxyethyl)-p-phenylenediamine sulfate monohydrate | 0.052 |
| 1,3-Dihydroxybenzene (resorcinol) | 0.563 |
| 1-Hydroxy-3-aminobenzene | 0.075 |
| 1,4-Diaminobenzene | 0.54 |
| 12-Hydroxystearic acid | 7.5 |
| Fragrance | 0.5 |
| Water | qs 100 |
| Glycerol | 3 |
| Vitamin C: ascorbic acid | 0.25 |

| Composition | B (comparative) |
|---|---|
| Ammonium hydroxide | 2.22 |
| Powdered sodium metabisulfite | 0.71 |
| Monoethanolamine | 1.2 |
| Ethylenediaminetetraacetic acid | 0.8 |
| Guanidine carbonate | — |
| 1-β-Hydroxyethyloxy-2,4-diaminobenzene dihydrochloride | 0.013 |
| N,N-Bis(2-hydroxyethyl)-p-phenylenediamine sulfate monohydrate | 0.052 |
| 1,3-Dihydroxybenzene (resorcinol) | 0.563 |
| 1-Hydroxy-3-aminobenzene | 0.075 |
| 1,4-Diaminobenzene | 0.54 |
| Fragrance | 0.95 |
| Water | qs 100 |
| Vitamin C: ascorbic acid | 0.25 |
| (Untreated anatase) titanium oxide coated with polydimethylsiloxane (98/2) | 0.15 |
| Glycol distearate | 2 |
| Cetylstearyl alcohol (50/50 C16/C18) | 11.5 |
| Hydrophobic fumed silica surface-treated with dimethylsilane | 1.2 |
| Poly[(dimethylimino)-1,3-propanediyl(dimethylimino)-1,6-hexanediyl dichloride] | 2.4 |
| Dimethyldiallylammonium chloride/acrylic acid (80/20) copolymer as an aqueous solution | 1.215 |
| Carboxyvinyl polymer synthesized in an ethyl acetate/cyclohexane mixture | 0.4 |
| Propylene glycol | 10 |
| Lauric acid | 3 |
| Oxyethylenated lauryl alcohol (12 units of ethylene oxide (EO)) | 7 |
| Oxyethylenated decyl alcohol (3 EO) | 10 |
| Oxyethylenated oleocetyl alcohol (30 EO) | 4 |

Compositions C and D according to the invention were also prepared using the ingredients below.

| Composition | C (invention) | D (invention) |
|---|---|---|
| Ammonium hydroxide | 2 | 2 |
| Powdered sodium metabisulfite | 0.7 | 0.7 |
| Monoethanolamine | 3 | 3 |
| Ethylenediaminetetraacetic acid | 0.2 | 0.2 |
| Guanidine carbonate | 0.8 | — |
| 1-β-Hydroxyethyloxy-2,4-diaminobenzene dihydrochloride | 0.013 | 0.013 |
| N,N-Bis(2-hydroxyethyl)-p-phenylenediamine sulfate monohydrate | 0.052 | 0.052 |
| 1,3-Dihydroxybenzene (resorcinol) | 0.563 | 0.563 |
| 1-Hydroxy-3-aminobenzene | 0.075 | 0.075 |
| 1,4-Diaminobenzene | 0.54 | 0.54 |
| 12-Hydroxystearic acid | 15 | 15 |
| Fragrance | 0.5 | 0.5 |
| Water | qs 100 | qs 100 |
| Glycerol | 3 | 3 |
| Vitamin C: ascorbic acid | 0.25 | 0.25 |

An oxidizing composition was prepared using the ingredients below.

| Oxidizing composition | Amount |
|---|---|
| Glycerol | 0.5 |
| (50% linear 70/30 C13/C15)alkyl ether carboxylic acid monoethanolamide (2 EO) | 0.85 |
| Tetrasodium pyrophosphate | 0.02 |
| Hydrogen peroxide | 6 |
| Sodium stannate | 0.04 |
| Diethylenetriaminepentaacetic acid, pentasodium salt | 0.06 |
| Cetylstearyl alcohol/oxyethylenated cetylstearyl alcohol mixture (30 EO) | 2.85 |
| Water | qs 100 |

Protocol:

Composition A according to the invention and the comparative composition B are mixed with one and a half times their weight of oxidizing composition (6% by weight of hydrogen peroxide).

Each mixture obtained is applied to locks of natural hair containing 90% grey hairs (NG), at a rate of 15 g of mixture per 1 g of hair.

After a leave-on time of 30 minutes at 27° C., the hair is rinsed with water, washed with a standard shampoo and then dried.

Rinseability Test:

For each of the compositions A and B, ten locks were dyed according to the protocol described above.

For each of the compositions A and B, ten experts evaluated the rinseability according to the protocol detailed below, each expert evaluating the rinseability of a lock.

The lock is placed a first time vertically under a tap of water at a temperature of 35° C., with a flow rate of 2 litres/min, for 5 seconds. This corresponds to a first passage. The rinseability evaluation is then performed according to the grading defined below, by placing the lock on absorbent paper.

The lock is placed a second time vertically under a tap of water at 35° C., with a flow rate of 2 litres/min, for 5 seconds, followed by wringing lightly between two triangular magnets out of the stream of water. This corresponds to a second passage. The rinseability evaluation is again performed by placing the lock on absorbent paper.

The latter operation is repeated twice to have a total of four passages, with a rinseability evaluation at each passage. The rinseability is given a score after each passage as follows:

0: a lot of composition remains on the lock
1: little composition remains on the lock
2: no composition remains on the lock, the lock needs to be opened to see composition on the interior
3: no composition remains when the lock is opened, it needs to be wrung vigorously to make composition come out
4: the lock is rinsed.

The scores obtained on each passage are then added together so as to obtain a final score: the higher the final score, the better the rinseability.

The results expressed as averages of the 10 final scores for each of the compositions A and B are as follows.

|  | Average score after four passages |
|---|---|
| Composition A (invention) | 3.7 |
| Composition B (comparative) | 1.8 |

Composition A according to the invention has markedly better rinseability than the comparative composition B representing a commercially available similar formulation.

Thus, composition A according to the invention makes it possible to reduce the rinsing time, and thus to reduce the amount of water required for optimum rinsing, relative to the comparative composition B.

Colorimetric Results:

The colouring of the locks treated with each of the compositions A and B according to the protocol described previously is evaluated by means of a Minolta 2600D spectrocolorimeter (D65 illuminant, angle 10°, specular component included) in the CIELab system.

In this system, L* represents the lightness: the lower the value of L*, the more intense and powerful the colouring obtained.

The component a* represents the red/green axis and the component b* represents the yellow/blue axis.

|  | Composition A (invention) | Composition B (comparative) |
|---|---|---|
| L* | 21.1 | 23.2 |

Composition A according to the invention has a lower L* value than the comparative composition B, and thus more intense, more powerful colouring than that of the comparative composition.

Measurement of the Viscosity of the Compositions:

Flow curves are produced using an MCR 502 rotary rheometer from Anton Paar, equipped with a Peltier air conditioning module to adjust the temperature to 25.0° C. A cone/plate geometry with a diameter of 50 mm/1° (5 μm sanded steel) was used, along with an anti-evaporation device so as to prevent evaporation during the measurement. The measurement protocol is as follows:

The flow curve was established using imposed shear rates $\gamma$ at 1; 10; 100 and 1000 $s^{-1}$ over respective durations of 10; 5; 2 and 0.5 min. The closer the shear-thinning slope is to −1, the greater the shear thinning and thus the easier the dye compositions are to apply and to spread on the hair.

| Formulation | Composition A (invention) | Composition B (comparative) |
|---|---|---|
| Shear-thinning slope | −0.75 ± 0.05 | −0.60 ± 0.05 |

Composition A according to the invention has a shear-thinning slope closer to −1 than comparative composition B. Thus, the composition of the invention is easier to use, i.e. easier to apply and to spread on the hair.

Stability Test at 60° C.

Compositions A and B are stored in an oven at 60° C. for 5 hours. After returning to room temperature, the macroscopic appearance is compared by visual observation and the microscopic appearance by light microscopy, between the compositions before storage at 60° C. and after storage.

Composition A according to the invention conserves the same macroscopic appearance before and after storage at 60° C., and the structure observed by light microscopy is not modified, whereas for comparative composition B, phase separation is observed after storage at 60° C. and the structures under light microscopy are modified. Composition A according to the invention is thus stable after storage at 60° C. and returning to room temperature, unlike the comparative composition B.

Example 2:

The dye composition A according to the invention and a comparative composition E are prepared using the ingredients indicated in the following table. The amounts indicated are expressed as weight percentages of active material relative to the total weight of the dye composition.

| Composition | A (invention) | E (comparative) |
|---|---|---|
| Ammonium hydroxide | 2 | 2 |
| Powdered sodium metabisulfite | 0.7 | 0.7 |

-continued

| Composition | A (invention) | E (comparative) |
|---|---|---|
| Monoethanolamine | 3 | 3 |
| Ethylenediaminetetraacetic acid | 0.2 | 0.2 |
| Guanidine carbonate | 0.8 | 0.8 |
| 1-β-Hydroxyethyloxy-2,4-diaminobenzene dihydrochloride | 0.013 | 0.013 |
| N,N-Bis(2-hydroxyethyl)-p-phenylenediamine sulfate monohydrate | 0.052 | 0.052 |
| 1,3-Dihydroxybenzene (resorcinol) | 0.563 | 0.563 |
| 1-Hydroxy-3-aminobenzene | 0.075 | 0.075 |
| 1,4-Diaminobenzene | 0.54 | 0.54 |
| 12-Hydroxystearic acid | 7.5 | — |
| Fragrance | 0.5 | 0.5 |
| Water | qs 100 | qs 100 |
| Glycerol | 3 | 3 |
| Vitamin C: ascorbic acid | 0.25 | 0.25 |

An oxidizing composition was prepared using the ingredients below (amounts indicated are expressed as weight percentages of active material relative to the total weight of the dye composition).

| Oxidizing composition | Amount |
|---|---|
| Glycerol | 0.5 |
| (50% linear 70/30 C13/C15) alkyl ether carboxylic acid monoethanolamide (2 EO) | 0.85 |
| Tetrasodium pyrophosphate | 0.02 |
| Hydrogen peroxide | 6 |
| Sodium stannate | 0.04 |
| Diethylenetriaminepentaacetic acid, pentasodium salt | 0.06 |
| Cetylstearyl alcohol/oxyethylenated cetylstearyl alcohol mixture (30 EO) | 2.85 |
| Water | qs 100 |

Composition A according to the invention and the comparative composition E are mixed with one and a half times their weight of the oxidizing composition containing 6% by weight of hydrogen peroxide.

Measurement of the Viscosity of the Compositions:

Flow curves are produced using an MCR 502 rotary rheometer from Anton Paar, equipped with a Peltier air conditioning module to adjust the temperature to 25.0° C. A cone/plate geometry with a diameter of 50 mm/1° (5 μm sanded steel) was used, along with an anti-evaporation device so as to prevent evaporation during the measurement. The measurement protocol is as follows:

The flow curve was established using imposed shear rates $\dot{\gamma}$ at 1; 10; 100 and 1000 $s^{-1}$ over respective periods of 10; 5; 2 and 0.5 min.

The closer the shear-thinning slope is to −1, the higher the shear-thinning and thus the easier the dye compositions are to apply and to spread on the hair.

The lower the viscosity at a given shear rate, the more fluid the dye compositions and the greater the risk of running on the head.

The results are detailed in the table below:

| Formulation | Composition A (invention) | Composition E (comparative) |
|---|---|---|
| Shear-thinning slope | −0.74 ± 0.05 | −0.25 ± 0.05 |
| Viscosity at 10 $s^{-1}$ (Pa · s) | 1.09 | 0.0018 |

Composition A according to the invention has a shear-thinning slope closer to −1 than comparative composition E. Thus, the composition of the invention is easier to use, i.e. easier to apply and to spread on the hair.

Furthermore, composition A according to the invention has a viscosity value at a shear rate of 10 $s^{-1}$ which is 600 times higher than that of comparative composition E at the same shear rate. Thus, the composition of the invention has less risk of running on the head.

The invention claimed is:

1. A dye composition comprising:
   12-hydroxystearic acid,
   at least one organic amine, and
   at least one dye chosen from oxidation dyes or direct dyes.

2. The dye composition according to claim 1, wherein the 12-hydroxystearic acid is present in an amount ranging from 0.1% to 40% by weight, relative to the total weight of the dye composition.

3. The dye composition according to claim 1, wherein the at least one organic amine is chosen from monoethanolamine (MEA), diethanolamine, triethanolamine, monoisopropanolamine, diisopropanolamine, guanidine carbonate, or mixtures thereof.

4. The dye composition according to claim 1, wherein the at least one organic amine is present in an amount ranging from 0.1% to 20% by weight, relative to the total weight of the dye composition.

5. The dye composition according to claim 1, wherein the at least one dye is chosen from at least one oxidation dye, and optionally at least one direct dye.

6. The dye composition according to claim 1, wherein the at least one dye is chosen from para-phenylenediamines, para-aminophenols, pyrazole derivatives, meta-phenylenediamines. meta-aminophenols, meta-diphenols, or mixtures thereof.

7. The dye composition according to claim 1, wherein the at least one dye is present in an amount ranging from 0.0001% to 20% by weight, relative to the total weight of the dye composition.

8. The dye composition according to claim 1, further comprising water in amount ranging from 20% to 95% by weight, relative to the total weight of the dye composition.

9. The dye composition according to claim 1, further comprising at least one alkaline agent other than organic amines, chosen from aqueous ammonia, sodium or potassium hydroxide, sodium or potassium carbonate, sodium or potassium bicarbonate, or mixtures thereof.

10. The dye composition according to claim 9, wherein the at least one alkaline agent other than organic amines is present in an amount ranging from 0.01% to 30% by weight, relative to the total weight of the dye composition.

11. A process for preparing a cosmetic composition, comprising:
   mixing 12-hydroxystearic acid, at least one organic amine, and at least one dye,
   optionally heating the mixture for a period of time ranging from 1 to 10 minutes at a temperature ranging from 60 to 70° C., with or without stirring, and
   cooling the mixture to room temperature.

12. A ready-to-use composition resulting from the extemporaneous mixing a dye composition (A) comprising 12-hydroxystearic acid, at least one organic amine, and at least one dye chosen from oxidation dyes or direct dyes, with an oxidizing composition (B) comprising at least one oxidizing agent.

13. The ready-to-use composition according to claim 12, wherein the oxidizing composition (B) comprises the least one oxidizing agent in an amount ranging from 0.1% to 20% by weight, relative to the total weight of the oxidizing composition (B).

14. The ready-to-use composition according to claim 13, wherein the at least one oxidizing agent is hydrogen peroxide.

15. A multi-compartment device for dyeing keratin fibers, comprising at least two compartments, wherein:

the first compartment contains a dye composition (A) comprising 12-hydroxystearic acid, at least one organic amine, and at least one dye chosen from oxidation dyes or direct dyes; and the second compartment contains an oxidizing composition (B) comprising at least one oxidizing agent.

16. A process for dyeing keratin fibers, the process comprising applying to the fibers a dye composition comprising:

12-hydroxystearic acid, at least one organic amine, and at least one dye chosen from oxidation dyes or direct dyes.

17. A process for dyeing keratin fibers, the process comprising applying to the fibers a ready-to-use composition resulting from the extemporaneous mixing a dye composition (A) comprising 12-hydroxystearic acid, at least one organic amine, and at least one dye chosen from oxidation dyes or direct dyes, with an oxidizing composition (B) comprising at least one oxidizing agent.

* * * * *